United States Patent [19]
Martin et al.

[11] Patent Number: 5,235,235
[45] Date of Patent: Aug. 10, 1993

[54] MULTIPLE-FREQUENCY ACOUSTIC WAVE DEVICES FOR CHEMICAL SENSING AND MATERIALS CHARACTERIZATION IN BOTH GAS AND LIQUID PHASE

[75] Inventors: Stephen J. Martin; Antonio J. Ricco, both of Albuquerque, N. Mex.

[73] Assignee: The United States of America as Represented by the United States Department of Energy, Washington, D.C.

[21] Appl. No.: 705,408

[22] Filed: May 24, 1991

[51] Int. Cl.$^5$ .......................................... H01L 41/08
[52] U.S. Cl. ............................. 310/313 D; 310/313 B; 73/23.27
[58] Field of Search ........... 310/313 B, 313 D, 313 R; 73/23.27, 24.06, 579, DIG. 4

[56] References Cited

U.S. PATENT DOCUMENTS

| | | | |
|---|---|---|---|
| 2,912,854 | 11/1959 | Schubring | 73/67.7 |
| 3,938,424 | 9/1976 | Parks | 310/8.1 |
| 4,096,740 | 6/1978 | Sallee | 73/88.5 R |
| 4,265,124 | 5/1981 | Lim et al. | 73/703 |
| 4,295,102 | 10/1981 | Schmidt et al. | 331/65 |
| 4,312,228 | 1/1982 | Wohltjen | 73/597 |
| 4,361,026 | 11/1982 | Muller et al. | 73/24.01 |
| 4,535,632 | 8/1985 | Sinha et al. | 73/DIG. 4 |
| 4,598,224 | 7/1986 | Ballato | 310/313 R |
| 4,609,843 | 9/1986 | Carr et al. | 310/313 A |
| 4,726,225 | 2/1988 | Brace et al. | 73/204 |
| 4,733,122 | 3/1988 | Shinonaga et al. | 310/313 R |
| 4,759,210 | 7/1988 | Wohltjen | 73/23 |
| 4,818,348 | 4/1989 | Stetter | 204/1 T |
| 4,895,017 | 1/1990 | Pyke et al. | 73/23 |
| 5,012,668 | 5/1991 | Haworth | 73/24.06 |
| 5,076,094 | 12/1991 | Frye et al. | 73/24.06 |
| 5,117,146 | 5/1992 | Martin et al. | 73/24.01 |

FOREIGN PATENT DOCUMENTS

| | | | |
|---|---|---|---|
| 0074920 | 3/1991 | Japan | 333/193 |
| 2182514 | 5/1987 | United Kingdom | 333/193 |

OTHER PUBLICATIONS

A. Ricco et al., "Surface Acoustic Wave Gas Sensor Based on Film Conductivity Changes", *Sensors and Actuators*, vol. 8, 1985, pp. 319-333.
G. Frye et al., "Monitoring Thin-Film Properties with Surface Acoustic Wave Devices: Diffusion, Surface Area, and Pore Size Distribution", *Chemical Sensors and Microinstrumentation*, American Chemical Society, Washington, D.C., 1989, pp. 208-221.
H. Wohltjen, "Mechanism of Operation and Design Considerations for Surface Acoustic Wave Device Vapour Sensors", *Sensors and Actuators* vol. 5, No. 4, 1984, pp. 307-325.
S. Martin et al., "Characterization of SH Acoustic Plate Mode Liquid Sensors", *Sensors and Actuators*, vol. 20, 1990, pp. 253-268.

*Primary Examiner*—Mark O. Budd
*Assistant Examiner*—Thomas M. Dougherty
*Attorney, Agent, or Firm*—Luis M. Ortiz; James H. Chafin; William R. Moser

[57] ABSTRACT

A chemical sensor (1) includes two or more pairs of interdigital electrodes (10) having different periodicities. Each pair is comprised of a first electrode (10a) and a second electrode (10b). The electrodes are patterned on a surface of a piezoelectric substrate (12). Each pair of electrodes may launch and receive various acoustic waves (AW), including a surface acoustic wave (SAW), and may also launch and receive several acoustic plate modes (APMs). The frequencies associated with each are functions of the transducer periodicity as well as the velocity of the particular AW in the chosen substrate material. An AW interaction region (13) exists between each pair of electrodes. Circuitry (20, 40) is used to launch, receive, and monitor the propagation characteristics of the AWs and may be configured in an intermittent measurement fashion or in a continuous measurement fashion. Perturbations to the AW velocity and attenuation are recorded at several frequencies and provide the sensor response.

29 Claims, 3 Drawing Sheets

MULTIPLE-FREQUENCY ACOUSTIC WAVE DEVICES FOR CHEMICAL SENSING AND MATERIALS CHARACTERIZATION IN BOTH GAS AND LIQUID PHASE

The United States Government has rights in this invention pursuant to Contract No. DE-AC04-76DP00789 between the United States Department of Energy and American Telephone and Telegraph Company.

FIELD OF THE INVENTION

This invention relates generally to a chemical and physical sensing apparatus and method and, in particular, to sensors based on acoustic wave sensor technology.

BACKGROUND OF THE INVENTION

Acoustic wave devices have demonstrated utility in a variety of sensing applications, including gas and vapor detection as well as sensing species in liquids. A two-port acoustic wave sensor includes an input transducer for generating an acoustic wave, an interaction region in which the propagating wave interacts with the environment, and an output transducer for detecting the wave. When an acoustic mode has significant amplitude at the surface, its propagation characteristics can be altered by changes in material on or near the device surface. The cumulative effects of such an interaction over the propagation path of the acoustic wave result in changes in wave amplitude and phase delay at the output transducer. In the simplest cases, acoustic wave devices function as highly sensitive detectors of changes in surface mass, responding primarily to accumulated mass per unit area. Specific sensors are achieved by securing a film capable of immobilizing a particular species from the environment to the interaction region of the device.

Reference is made to the following journal articles and U.S. patents as teaching various aspects of acoustic wave devices.

An article entitled "Characterization of SH Acoustic Plate Mode Liquid Sensors", by S. J. Martin, A. J. Ricco, T. M. Niemczyk, and G. C. Frye, SENSORS & ACTUATORS, Vol. 20, pp. 253-268 (1990) describes a two-port acoustic wave sensor that utilizes shear horizontal acoustic plate modes to probe a solid/liquid interface. The modes are excited and detected by interdigital transducers on thinned quartz plates.

In an article entitled "Monitoring Thin-Film Properties with Surface Acoustic Wave Devices: Diffusion, Surface Area, and Pore Size Distribution", by G. C. Frye, S. J. Martin, A. J. Ricco, and C. J. Brinker, CHEMICAL SENSORS AND MICROINSTRUMENTATION, *American Chemical Society*, Washington, D. C. 1989, pp. 208-221, there is described an ability of surface acoustic wave devices to monitor an absorption of $N_2$ onto the surfaces of porous films and also the diffusion of species into polymer films.

In an article entitled "Mechanism of Operation and Design Considerations and Design Considerations for Surface Acoustic Wave Device Vapor Sensors", SENSORS & ACTUATORS, Vol. 5, pp. 307-325 (1984), H. Wohltjen describes characteristics of surface acoustic wave devices and techniques by which they may be employed as vapor sensors. The perturbation of surface acoustic wave velocity by polymeric coating films is also discussed. The article states that highest sensitivity can be achieved when the device is used as the resonating element in a delay line oscillator circuit.

In an article entitled "Surface Acoustic Wave Gas Sensor Based on Film Conductivity Changes", SENSORS & ACTUATORS, Vol. 8, pp. 319-333 (1985) by A. J. Ricco, S. J. Martin, and T. E. Zipperian there is described a surface acoustic wave sensor that functions via changes in the conductivity of a thin surface film.

U.S. Pat. No. 4,895,017, issued Jan. 23, 1990, entitled "Apparatus and Method for Early Detection and Identification of Dilute Chemical Vapors" to Pyke et al. describes a detector and method for identifying a chemical vapor and determining its concentration. The chemical detector includes a plurality of surface acoustic wave devices.

U.S. Pat. No. 4,726,225, issued Feb. 23, 1988 entitled "Surface Acoustic Wave Gas Flow Rate Sensor with Self-Heating Feature" to Brace et al. describes a surface acoustic wave device for measuring a mass flow rate of a gas. The surface acoustic wave device includes a surface acoustic wave delay line formed of a piezoelectric substrate.

In U.S. Pat. No. 4,598,224, issued Jul. 1, 1986 entitled "Surface Acoustic Wave Device for Sensing the Presence of Chemical Agents" Ballato describes a surface acoustic wave device for sensing the presence of chemical agents by chemo-electronic means.

U.S. Pat. No. 4,312,228, issued Jan. 26, 1982, entitled "Methods of Detection with Surface Acoustic Wave and Apparatus Therefor" to Wohltjen describes the monitoring of physical parameters relating to various fluids and polymers by contacting same with the surface of a piezoelectric material through which is passing a surface acoustic wave. An alteration of the wave is said to be an indication of the parameters.

U.S. Pat. No. 4,265,124 issued May 5, 1981, entitled "Remote Acoustic Wave Sensors" by Lim et al. describes an acoustic wave sensor that includes an acoustic wave oscillator having a resonant frequency that is modulated according to changes in a physical variable.

U.S. Pat. No. 4,096,748, issued Jun. 27, 1978 entitled "Surface Acoustic Wave Strain Detector and Gage" to Sallee describes a strain sensor that includes an oscillator having a surface acoustic wave delay line as a frequency controlled element.

The following patents are cited as being of general interest in the area of sensor technology.

U.S. Pat. No. 4,818,348, issued Apr. 4, 1989, entitled "Method and Apparatus for Identifying and Quantifying Simple and Complex Chemicals" to Stetter discloses the use of a computer controlled array of chemical sensors. U.S. Pat. No. 4,295,102, issued Oct. 13, 1981, entitled "Surface Acoustic Wave Sensor Sensing Circuits" to Schmidt et al. describes a surface acoustic wave sensor system in which a predetermined level of coupling between two surface acoustic wave arrays is intentionally provided so as to couple RF energy from one into the other. U.S. Pat. No. 4,759,210, issued Jul. 26, 1988 entitled "Apparatus for Gas-Monitoring and Method of Conducting Same" by Wohltjen et al. describes a method of monitoring a gas that includes trapping means, such as a tube or other conduit, through which the gas to be monitored is passed. A sorbent mass is provided to intercept the gas passing through the conduit. Chemical sensors are provided in an array for monitoring the gas after it emerges from a conduit. U.S. Pat. No. 3,983,424, issued Sep. 28, 1976, entitled "Radiation Detector Employing Acoustic Surface Waves" to Parks describes a radiation detector having an acoustic transmission line with transducers on a substrate for providing an acoustic surface wave in the substrate. A phase change in the wave is said to be a measure of the temperature change, resulting from absorbed radiation, at the surface of the substrate. Finally, U.S. Pat. No. 2,912,854, issued Nov. 17, 1959, entitled "Ultrasonic Surface Testing Device" to Schubring describes a surface testing device that employs ultrasonic energy.

What is not taught by this prior art, and what is thus an object of the invention to provide, is a multiple-frequency surface acoustic wave device for chemical sensing and materials characterization in both gas and liquid phase.

It is a further object of the invention to provide method and apparatus to detect the presence and/or concentration of a chemical species or substance in the gas or liquid phase, or to characterize one or more physical properties of a thin film of material, by employing an acoustic wave (AW) sensor that operates simultaneously or sequentially at a plurality of distinct frequencies.

It is one further object of the invention to provide a multiple-frequency AW sensor operable for differentiating a response due to one physical perturbation from the response due to another physical perturbation.

SUMMARY OF THE INVENTION

The objects of the invention are realized by an apparatus and method employing a multiple-frequency AW sensor for detecting a presence and/or concentration of a chemical species or substance in the gas or liquid phase, or to characterize one or more physical properties of a thin film of material. The invention employs an acoustic wave (AW) device which operates simultaneously or sequentially at several distinct frequencies.

The configuration of a multiple-frequency AW sensor differs from the conventional AW sensors described above in that the response to a given stimulus is recorded at more than one frequency. The stimulus may be, by example, the reaction, binding, or sorption of a species to be detected on the sensor surface. In general, any change in a physical property of the AW device surface or near-surface region which affects the acoustic wave velocity or attenuation may be exploited to construct a sensor. Measuring the response to a perturbation at multiple frequencies relies on a property of the AW sensor that perturbations, such as changes in surface mass, elasticity, conductivity, viscosity, etc., often differ in their dependence upon frequency. The multiple-frequency AW device of the invention differentiates between responses resulting from different physical perturbations. This differentiation of perturbation sources is most often not possible using a single-frequency AW sensor device of the prior art.

More specifically, a chemical or physical sensor includes two or more pairs of interdigital electrodes having different periodicities. Each pair is comprised of a first set electrodes and a second set of electrodes. The electrodes are patterned on a surface of a piezoelectric substrate. Each pair of electrodes may launch and receive various acoustic waves, including a surface acoustic wave, and may also launch and receive several acoustic plate modes. The frequencies associated with each acoustic wave are functions of the transducer periodicity as well as the velocity of the particular AW in the chosen substrate material. An AW interaction region exists between each pair of electrodes. Circuitry is used to launch, receive, and monitor the propagation characteristics of the AWs and may be configured in an intermittent measurement fashion or in a continuous measurement fashion. Perturbations to the AW velocity and attenuation are recorded at several frequencies and provide the sensor response.

BRIEF DESCRIPTION OF THE DRAWINGS

The above set forth and other features of the invention are made more apparent in the ensuing Detailed Description of the Invention when read in conjuction with the attached Drawings, wherein.

DETAILED DESCRIPTION OF THE INVENTION

Figure 1:
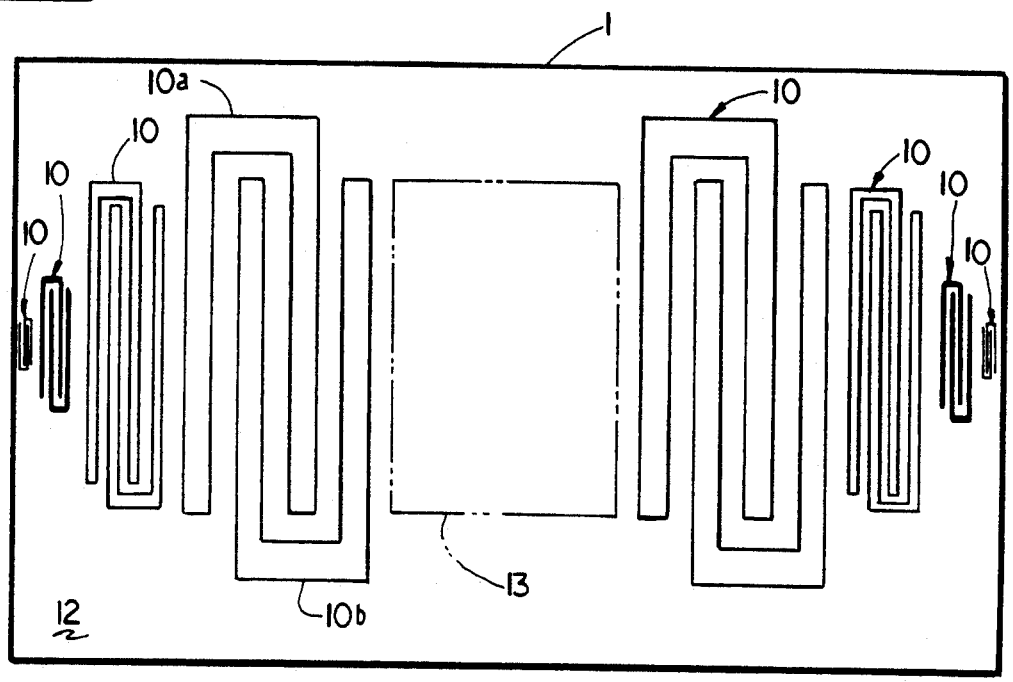
FIG. 1 is a simplified schematic diagram of multiple frequency AW sensor constructed and operated in accordance with the invention.

Referring to FIG. 1 there is illustrated an embodiment of a sensor 1. Sensor 1, as described in detail below, includes two or more pairs of interdigital electrodes or transducers (IDTs) 10 having different periodicities. Each IDT 10 is comprised of a first electrode 10a and a second electrode 10b, as shown. The IDTs 10 are patterned on a surface of a piezoelectric substrate 12. Each pair of IDTs 10 may launch and receive various AWs, including a surface acoustic wave (SAW), also known in the art as a Rayleigh wave, and may also launch and receive several acoustic plate modes (APMs). The frequencies associated with each are functions of the transducer periodicity as well as the velocity of the particular AW in the chosen substrate 12 material. By example, input and output transducers include 25 pairs of interdigitated electrodes for the larger (16 MHz and 40 MHz) transducers 10, and 50 pairs of interdigitated electrodes for the smaller (100 MHz and 250 MHz) transducers 10. The AW interaction region 13 is indicated in FIG. 1 by the dashed box.

The SAW is typically chosen for gas-phase and materials-characterization applications where no liquid contacts the surface and where a maximum mass sensitivity is desired, while the shear-horizontal APM (SH-APM) is chosen for liquid-phase applications. For more detailed disclosure of liquid-phase applications, see U.S. patent application Ser. No. 187,776, filed Apr. 29, 1988, entitled "Acoustic Wave Device Using Plate Modes With Surface-Parallel Displacement," by Martin and Ricco (same inventors as herein), which application is hereby incorporated by reference. Electronic test and measurement circuitry used to launch, receive, and monitor the propagation characteristics of the AWs can be configured in several embodiments, two of which are described below in reference to FIGS. 3 and 4. Both of these configurations allow both the velocity and the attenuation of the AW to be measured at all of the frequencies defined by the various transducers 10. For a detailed disclosure relating to simultaneous measurement of attenuation and velocity, see U.S. patent application Ser. No. 592,383, filed Oct. 3, 1990, entitled "Dual Output Acoustic Wave Sensor for Molecular Identification," to Frye and Martin, which application is hereby incorporated by reference. Perturbations to the AW velocity and attenuation which result from either: (a) the interaction of a detectable chemical species with the AW sensor surface; or (b) a change in the physical nature of a thin film during a change in ambient conditions, such as temperature, gas pressure, concentration of a vapor, etc., are thus recorded at several frequencies and provide the sensor response.

EXAMPLE

A multiple-frequency AW device was fabricated on ST-cut quartz with nominal SAW center frequencies of 16, 40, 100, and 250 MHz and nominal SH-APM center frequencies of 25.6, 64, 160, and 400 MHz. The four frequencies were obtained by patterning four sets of interdigital transducers 10 having periodicities of 200, 80, 32, and 12.8 $\mu$m, respectively, on a single ST-quartz substrate 12, as depicted schematically in FIG. 1. The input transducers are those on the left of FIG. 1; the output transducers are those on the right.

In greater detail, the interdigital transducers 10 were fabricated on a 0.5 mm thick ST-cut quartz wafer. The transducers 10 were defined photolithographically, using an etching process, from 100 to 200 mm thick Au-on-Cr metallization. Wafers were diamond sawed into 3.6×1.3 cm devices, each of which was then attached to an alumina PC board having a number of 50 ohm lithographically defined coplanar-waveguides running from the sensor 1 to contact areas along the board's periphery. Wire bonds of 25 $\mu$m Au were made between transducer 10 bonding pads and the waveguides. In some cases, several input transducers having different periodicity were bonded in parallel to a single guide; corresponding output transducers were then similarly connected in parallel. PC board-mounted devices were installed in a brass test case utilizing Au-plated Cu/Be spring contacts to connect the board's contact pads to jacks, which were connected by coaxial cable to the external circuitry.

TABLE

DESIGN PARAMETERS FOR MULTIFREQUENCY ACOUSTIC WAVE DEVICE

| | | | | |
|---|---|---|---|---|
| SAW Center Frequency, MHz | 16 | 40 | 100 | 250 |
| Acoustic Wavelength, $\mu$m | 200 | 80 | 32 | 12.8 |
| No. of Finger Pairs | 25 | 25 | 50 | 50 |
| Acoustic beam width, $N\Lambda_o.1$ | 50 | 100 | 100 | 100 |
| Acoustic path length, $N\Lambda_o.2$ | 75 | 280 | 850 | 2400 |

In the Table set forth above $N\Lambda_o1$ equals the length of transducer fingers in acoustic wavelengths and $N\Lambda_o2$ equals the center-to-center spacing between input and output transducers in acoustic wavelengths.

Figure 2:
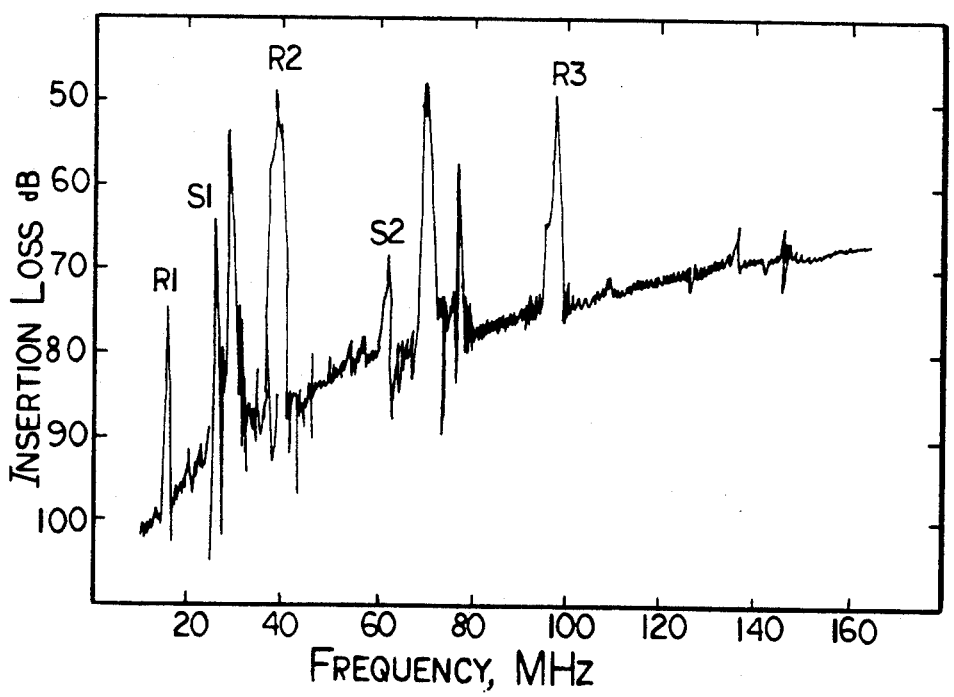
FIG. 2 depicts the frequency response of the multi-frequency AW sensor of FIG. 1.

Frequency response data for the multi-frequency AW sensor of FIG. 1 is shown in FIG. 2. The frequency response reveals SAW peaks (denoted R for Rayleight wave) at approximately 15.5, 39.3, and 97.2 MHz and SH-APM peaks (denoted S) at approximately 24.5 and 62.1 MHz. Peaks at 160, 250, and 400 MHz are not shown in FIG. 2. Various other acoustic plate modes are apparent as well. Measurements of the mass sensitivity ($c_m$) of the SAWs shows a known dependence on frequency (f), given by $c_m \propto f$, where the measured response is $\Delta f/f$. In addition, measurements of changes in thin metal film conductivity via acoustoelectric coupling show the expected frequency independence of the magnitude of this effect, i.e. $\Delta f/f \propto \Delta v/v \propto K^2$, where v and $K^2$ represent the frequency-invariant SAW velocity and electromechanical coupling coefficient, respectively.

Figure 3:
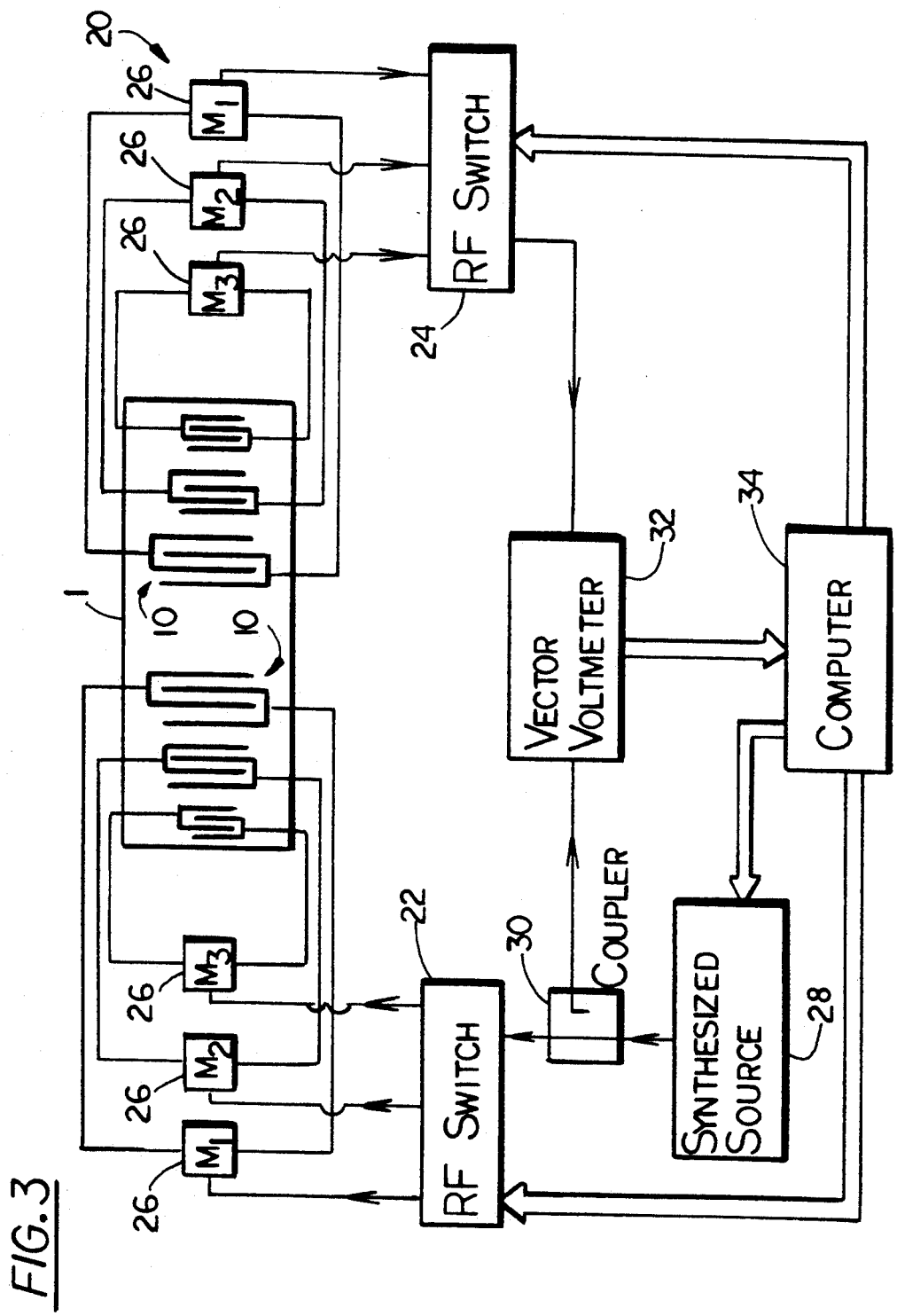
FIGS. 3 and 4 each show a simplified schematic diagram of an electronic measurement configuration for multiple-frequency AW sensors, specifically, a sequential measurement configuration and a simultaneous measurement configuration, respectively.

FIG. 3 shows a first configuration of electronic apparatus 20 for measuring changes in AW velocity and attenuation at multiple frequencies. For the purpose of illustration, three different sets of IDTs 10 are shown; however extension to a larger number of frequencies is straightforward. The embodiment of FIG. 3 measures v and $\alpha$ at each of the transducer frequencies in rapid sequence using two RF switches 22 and 24, while the configuration of FIG. 4, described in detail below, measures these parameters simultaneously. The impedance matching networks, labelled $M_i$, are indicated by the numeral 26.

For the multiplexed configuration of FIG. 3 each pair of input and output IDTs 10 is connected in rapid sequence through the RF switches 20 and 22 to a synthesized source 28 and, via a 10 dB coupler 30, to a vector voltmeter 32. Switching is accomplished under control of a computer 34. The computer 34 also controls the operation of the source 28 and the vector voltmeter 32.

The multiplexed configuration of FIG. 3 is operated by one of two methods. A first method employs a fixed frequency, corresponding to the center frequency for either the SAW or the APM, as appropriate. The fixed frequency is applied to the appropriate input transducer 10 using the synthesizer 28. The vector voltmeter 32 measures changes in the AW phase difference and amplitude between the input and output IDTs 10, giving the corresponding changes in v and $\alpha$. This measurement is repeated at each of the multiple frequencies as the RF switches 22 and 24 are cycled through the pairs of IDTs 10.

A second method operates the circuitry of FIG. 3 in a manner similar to a phase-locked loop. Specifically, the synthesizer 28 frequency for each IDT pair is adjusted sequentially by the computer 34 to maintain a constant phase difference between the selected pair of IDTs. The synthesizer 28 frequency is thus a measure of the change $\Delta$ v, while changes in $\alpha$ are recorded using the vector voltmeter 32, as before.

Figures 4, 4A:
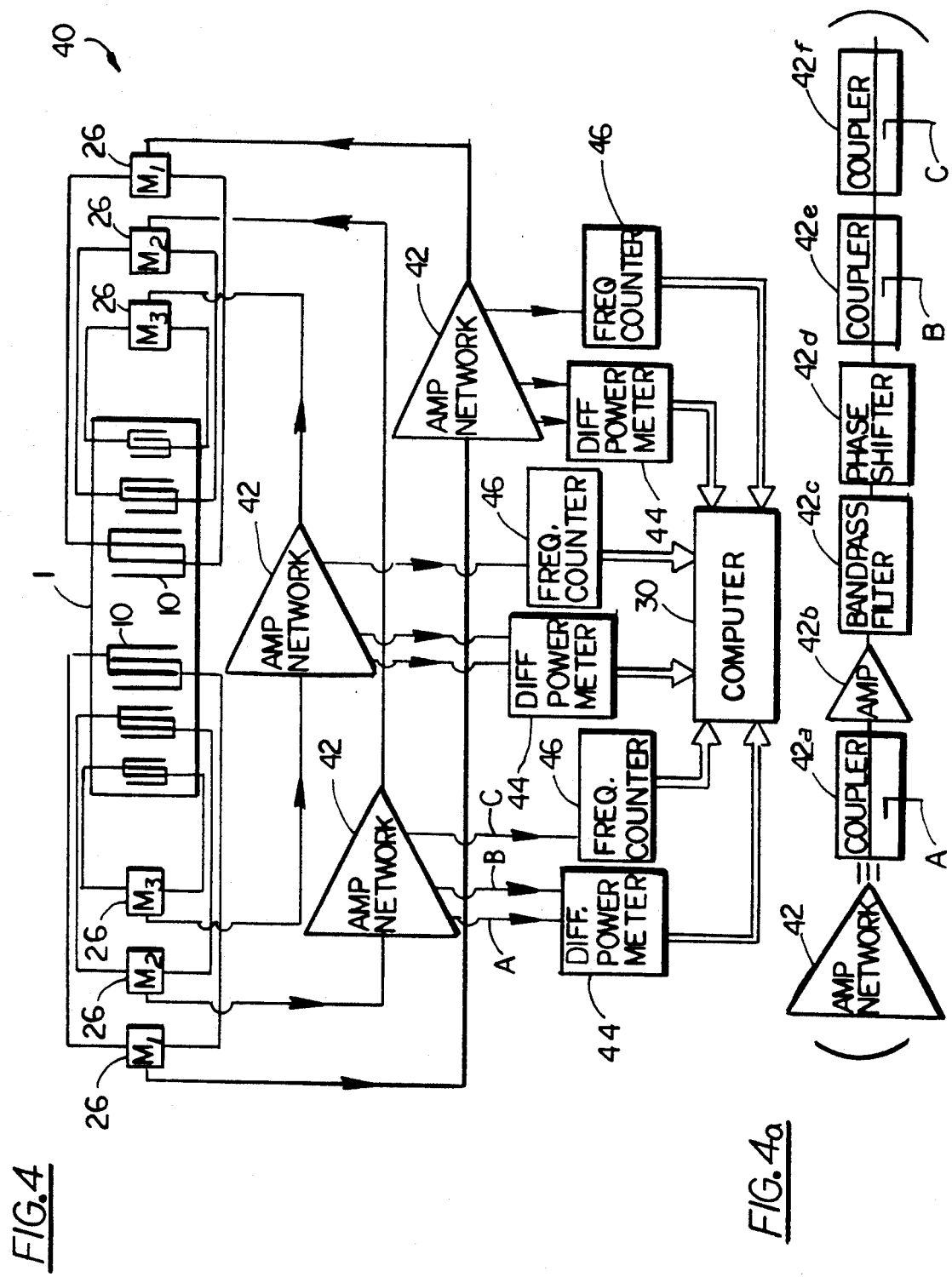
FIG. 4a is a simplified schematic diagram showing in greater detail an amplifier network that is a feature of the embodiment shown in FIG. 4.

FIG. 4 shows a second configuration of electronic apparatus 40 for measuring changes in AW velocity and attenuation at multiple frequencies. Components labeled as in FIG. 3 operate in similar fashion. In the embodiment of FIG. 4 pairs of input and output IDTs 10 are connected into a feedback loop of an associated amplifier network 42, each functioning as a separate free-running oscillator circuit. Each amplifier network includes the components shown in FIG. 4a. Specifically these components include a first coupler 42a, an amplifier 42b, a bandpass filter 42c, a phase shifter 42d, a second coupler 42e and a third coupler 42f. These components are serially coupled together as shown with the couplers 42b, 42e and 42f providing output nodes A, B and C, respectively, for connection to a differential power meter 44 and a frequency counter 46.

The frequency of oscillation of each oscillator circuit is detected by an associated frequency counter 46 and is a measure of change in v, while changes in $\alpha$ are measured via the difference in AW amplitude at input and output transducers, using the differential power meter 44 or, if desired, a vector voltmeter.

Variations of the configurations shown in FIGS. 3, 4 and 4a are within the scope of the teaching of the invention. Thus, while the invention has been particularly shown and described with respect to exemplary embodiments thereof, it will be understood by those skilled in the art that changes in form and details may be made therein without departing from the scope and spirit of the invention.

What is claimed is:

1. A chemical or intrinsic physical property sensor comprising:
   (a) a substrate;
   (b) an interaction region of said substrate where the presence of a chemical or physical stimulus causes a detectable change in the velocity and/or an attenuation of an acoustic wave traversing said region; and
   (c) a plurality of paired input and output interdigitated electrodes patterned on the surface of said substrate where each of said paired interdigitated electrodes has a distinct periodicity, where each of said paired electrodes is comprised of an input interdigitated electrode and an output interdigitated electrode, and where said interaction region lies between said input interdigitated electrodes and said output interdigitated electrodes for all of said plurality of interdigitated electrodes;
   (d) an input signal generation means for transmitting an input signal having a distinct frequency to a specified input interdigitated electrode of said plurality so that each input interdigitated electrode receives a unique input signal, whereby said interdigitated electrode responds to said input signal by generating an acoustic wave of a specified frequency, thus, said plurality responds by generating a plurality of acoustic waves of different frequencies;
   (e) an output signal receiving means for determining an acoustic wave velocity and an amplitude of said acoustic waves at several frequencies after said waves transverses said interaction region and comparing these values to an input acoustic wave velocity and an input acoustic wave amplitude to produce values for perturbations in acoustic wave velocities and for acoustic wave attenuation as a function of frequency, where said output receiving means is individually coupled to each of said output interdigitated electrode;
   (f) a computer means for analyzing a data stream comprising information from said output receiving means and from said input signal generation means to differentiate a specified response due to a perturbation from a subsequent specified response due to a subsequent perturbation to determine the chemical or intrinsic physical properties desired.

2. A chemical or physical sensor as set forth in claim 1 wherein said substrate is comprised of a piezoelectric material.

3. A chemical or physical sensor as set forth in claim 1 wherein said substrate is comprised of ST-cut quartz.

4. A chemical or physical sensor as set forth in claim 1 wherein each of said interdigitated electrodes is comprised of a layer of metallization.

5. A chemical or physical sensor as set forth in claim 1 wherein said means for generating multiple distinct frequency signals applies said signals to said input means intermittently.

6. A chemical or physical sensor as set forth in claim 1 wherein said means for generating multiple distinct frequency signals applies said signals to said input means continuously.

7. A chemical or physical sensor as set forth in claim 1 wherein the output means of each of said pair is further coupled to a means for measuring a change in said distinct frequency signal coupled at said interaction region, the change being indicative of a chemical or physical stimulus.

8. The sensor of claim 1 whereby said interactive region comprises a film coupled to said substrate and capable of immobilizing a particular species from the environment.

9. The chemical sensor of claim 1 where said chemical stimulus is in the gas phase.

10. The chemical sensor of claim 1 where said chemical stimulus is in the liquid phase.

11. The intrinsic physical property sensor of claim 1 where said stimulus is a thin film of material to be analyzed.

12. The sensor of claim 1 wherein a perturbation determination means couples said input signal generation means and said output signal receiving means to said computer means, wherein said input signal generating means further comprises a first switching means, a synthesized source means and a coupler means where said coupler means is coupled to said perturbation determination means which also forms part of said output signal receiving means, and wherein said output signal receiving means further comprises a second switching means coupled to said perturbation means, wherein said perturbation means which is coupled to said computer means for generating and receiving acoustic waves in a sequential order resulting in the sequential interaction of acoustic waves of differing frequencies with an environment associated with said interactive region.

13. The sensor of claim 1 whereby said input interdigitated electrode and said output interdigitated electrode for each pair comprising said plurality is coupled to a distinct amplifier network means through a plurality of feedback loops for the simultaneous interaction of acoustic waves of differing frequencies with an environment associated with said interactive region, where said amplifier network is coupled to an wave attenuation means for determining an attenuation of said acoustic wave after traversing said interaction region and to an associated frequency counting means for determining a perturbation in the frequency of said acoustic wave after traversing said interaction region, where said attenuation means and said counting means are in turn are coupled to said computer means to determine the desired chemical and intrinsic physical parameters.

14. The sensor of claim 1 where each pair of said interdigitated electrodes forming said plurality is aligned along an axis which intersects said interaction region.

15. An acoustic wave chemical or physical sensor, comprising:
   (a) a substrate of material suitable for supporting an acoustic wave having a specific frequency therein; and
   (b) a plurality of input electrodes and a plurality of output electrodes disposed upon a surface of said substrate, where an input electrode comprising one electrode of said plurality of input electrodes corresponds to an output electrode comprising one electrode of said plurality of output electrodes to form an interdigitated pair, each component of said pair of interdigitated electrodes, said input electrode and said output electrode being responsive to generating and receiving respectively an acoustic wave having a distinct frequency range and a measurable amplitude for coupling a response of an acoustic wave to changes introduced in an interactive region:

(c) an interaction region defined by all of said paired electrodes where said interaction region is bounded on one side by said plurality of input interdigitated electrodes and on the other side by a plurality of said output interdigitated electrodes said input and said output interdigitated electrodes being spaced apart from one another upon the surface of said substrate;

(d) a plurality of oscillator circuit means for generating and receiving signals where a distinct oscillator means of said plurality generates and receives signals which fall within said distinct frequency range and where said distinct oscillator means couples said input electrode to said output electrode of a distinct pair of electrodes where said input interdigitated electrode is responsive to a generating signal from said oscillator means and where said output interdigitated electrode of said pair produces a receiving signal in response to a perturbed acoustic wave, said interaction region being a region where the presence of a chemical species or changes in the intrinsic physical properties of a thin film causes a detectable change in said frequency of said acoustic wave and/or an attenuation of said acoustic wave coupled between a pair of said interdigitated electrodes.

16. An acoustic wave chemical or physical sensor as set forth in claim 15 wherein the output of each of said pair of interdigitated electrodes is further coupled to means for measuring a change experienced by the acoustic wave coupled therebetween, a magnitude of said attenuation being indicative of a presence or a concentration of the chemical species or of a change or changes in the physical properties of a thin film in contact with the device surface.

17. An acoustic wave chemical or intrinsic physical property sensor comprising:

(a) a substrate suitable for supporting acoustic waves therein;

(b) a thin film sensitive to the presence of a chemical or a physical stimulus disposed on said substrate;

(c) an interaction region encompassing said thin film on said substrate where the presence of said stimulus changes properties of said thin film which causes a detectable change in the velocity and/or an attenuation of an acoustic wave which transverses the film; and (d) a plurality of paired input and output means disposed upon said substrate where each of said paired input and output means comprising said plurality has a distinct periodicity different from each of said other paired input and output means, where an input means of said pair is responsive to a means for generating acoustic waves where said generating means transmits a signal having a distinct frequency based on the periodicity of said input means to said input means, wherein said plurality of input means provides acoustic waves having multiple distinct frequencies to said interactive region, and said plurality of output means receives acoustic waves which have undergone a phase shift and/or a change in amplitude due to the presence of said stimulus in said interaction region and provides a response which is indicative of said shift or change an output measuring means, whereby each individual one of said paired input means has a corresponding output means, where each of said pairs is responsive to acoustic waves having distinct and different acoustic frequencies and where said output measuring means is coupled to said acoustic wave generating means and to a computing means for detecting a perturbation in acoustic wave velocity and an attenuation of said acoustic wave as a function of frequency to determine chemical or intrinsic physical properties of said stimulus.

18. An acoustic wave chemical or physical sensor as set forth in claim 1 wherein the input means of each of said pair is coupled to a means for intermittently applying a distinct frequency.

19. An acoustic wave chemical or physical sensor as set forth in claim 18 wherein the output of each of said pair of interdigitated electrodes is further coupled to means for measuring a change experienced by the acoustic wave coupled therebetween, a magnitude of said attenuation being indicative of a presence or a concentration of the chemical species of a change or changes in the intrinsic physical properties of a thin film contacted with the surface device surface.

20. A method of operating a multiple frequency chemical or intrinsic physical property sensing means, comprising the steps of:

(a) applying, from a multiple frequency source having multiple distinct frequency signals, a distinct frequency signal to each of a plurality of individual input means of the sensor;

(b) generating an acoustic wave having a distinct frequency specific to each input means comprising said plurality, said sensor having an individual output means corresponding to each individual input means wherein there is a one to one correspondence from each said individual input means to said individual output means forming a paired input and output means wherein an interaction region is defined between said input and output means;

(c) exposing said interaction region of said sensor to a chemical or physical stimulus that will change said specific frequency and/or said specific amplitude of said generated acoustic wave; and (d) receiving said generated acoustic wave at said paired output means, wherein each of said output means is at least responsive to the distinct frequency signal applied to its corresponding input means;

(e) determining a velocity and a amplitude perturbation for said acoustic wave between said generation and said reception as a function of frequency;

(e) analyzing said perturbations over a plurality of frequencies to determine chemical or intrinsic physical properties associated with said exposure of said interactive region to said chemical or physical stimulus.

21. A method as set forth in claim 20 wherein said step of applying a distinct frequency signal and said step of detecting are sequentially performed for each of the distinct frequency signals.

22. A method as set forth in claim 20 wherein said step of applying a distinct frequency signal and said step of detecting are simultaneously performed for each of the distinct frequency signals.

23. The method of claim 20 including securing a film capable of immobilizing a particular species from the environment to said interactive region of said sensor.

24. The method of claim 20 including operating said paired interdigitated electrodes simultaneously at a plurality of distinct frequencies.

25. The method of claim 20 including operating said paired interdigitated electrodes sequentially at a plurality of distinct frequencies.

26. The method of claim 20 including using computing means in analyzing perturbations in an acoustic wave velocity and in analyzing an attenuation of said acoustic wave at several frequencies to determine a chemical presence and/or a concentration when said stimulus is in a gas phase.

27. The method of claim 20 including using computing means in analyzing perturbations in an acoustic wave velocity and in analyzing an attenuation of said acoustic wave at several frequencies to determine a chemical presence and/or a concentration when said stimulus is in a liquid phase.

28. The method of claim 20 including using computer means in analyzing a perturbation in acoustic wave velocity and in analyzing an attenuation of said wave at several frequencies to determine intrinsic physical properties of a thin film where said thin film is coupled to said interactive region.

29. The method of claim 20 including selecting said paired input and output means in such a manner that a frequency range associated with said output means corresponds with a frequency range associated with said paired input means so that the output means reponds to the acoustic wave generated by its paired input means to eliminate signal overlap between said input and output means comprising said plurality.

* * * * *